United States Patent [19]

Salzburg et al.

[11] Patent Number: 4,683,233

[45] Date of Patent: Jul. 28, 1987

[54] SALTS OF 2-KETO-2H, 3H-1,2-BENZISOTHIAZOLE 1,1-DIOXIDE AS MICROBICIDES

[75] Inventors: Herbert Salzburg; Manfred Hajek, both of Cologne; Gerd Hänssler, Leverkusen; Varl-Heinz Kuck, Langenfeld, all of Fed. Rep. of Germany

[73] Assignee: Bayer Aktiengesellschaft, Leverkusen, Fed. Rep. of Germany

[21] Appl. No.: 704,439

[22] Filed: Feb. 22, 1985

[30] Foreign Application Priority Data

Mar. 8, 1984 [DE] Fed. Rep. of Germany ....... 3408538
Aug. 22, 1984 [DE] Fed. Rep. of Germany ....... 3430805

[51] Int. Cl.$^4$ ..................... A01N 43/40; A01N 43/60; A01N 43/80; A01N 43/84

[52] U.S. Cl. .................................... 514/253; 514/229; 514/256; 514/275; 514/300; 514/321; 514/373

[58] Field of Search ............... 514/373, 229, 253, 256, 514/275, 300, 321

[56] References Cited

U.S. PATENT DOCUMENTS

| | | | |
|---|---|---|---|
| 3,065,123 | 11/1962 | Hinton et al. | 514/373 |
| 3,325,465 | 6/1967 | Vacek | 260/211 |
| 3,839,571 | 10/1974 | Ciccone et al. | 514/373 |
| 3,970,755 | 7/1976 | Gazzard et al. | 514/373 |
| 4,291,045 | 9/1981 | Mackay et al. | 426/660 |

FOREIGN PATENT DOCUMENTS

| | | | |
|---|---|---|---|
| 49-117627 | 11/1974 | Japan | 514/373 |

OTHER PUBLICATIONS

Chemical Abstracts, vol. 80, No. 15, p. 83, Apr. 15, 1974, Abstract 79144h, "Nonmedical Germicides Containing 2-Pipecoline Saccharinate."

Chemical Abstracts, vol. 79, No. 19, Nov. 12, 1973, Abstract No. 112382p, "Germicidal Compositions Containing Saccharin Derivatives."

Chemical Abstracts, vol. 79, No. 13, Oct. 1, 1973, p. 159, Abstract 74918h, "Agrochemical Germicides Containing Saccharin Derivatives."

Chemical Abstracts, vol. 80, No. 3, Jan. 21, 1974, p. 104, Abstract 11212y, "Insecticides, Acaricides and Agricultural Germicides . . . ".

Chemical Abstracts, vol. 79, No. 13, Oct. 1, 1973, p. 161, Abstract 74938q, "Insecticides and Germicides Containing 1,3-bis(carbamylthio)-2-dimethyl . . . ".

(List continued on next page.)

*Primary Examiner*—Allen J. Robinson
*Attorney, Agent, or Firm*—Sprung Horn Kramer & Woods

[57] ABSTRACT

A method of combating fungi and bacteria which comprises applying to such fungi, bacteria or a habitat thereof, a fungicidally or bactericidally effective amount of at least one salt of 3-keto-2-, 3H-1,2-benzisothiazole 1,1-dioxide of the formula

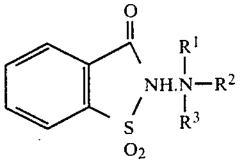

in which $R^1$ represents hydrogen, alkyl having 1 to 18 carbon atoms, or alkyl which has 1 to 6 carbon atoms and is optionally monosubstituted to trisubstituted by hydroxyl and/or monosubstituted to trisubstituted by amino, or represents carboxyl-substituted alkyl having 1 to 4 carbon atoms, or phenyl which is optionally monosubstituted to trisubstituted by identical or different substituents from amongst nitro and chlorine, or represents cycloalkyl having 5 or 6 carbon atoms, or represents heterocyclic structures which are optionally saturated or unsaturated, are optionally monosubstituted to tetrasubstituted by alkyl having 1 to 4 carbon atoms or hydroxyl, and have 1 to 3 identical or different heteroatoms, and a total of 5 or 6 ring members, $R^2$ represents alkyl having 1 to 18 atoms, or alkyl which has 1 to 6 carbon atoms and is optionally monosubstituted to trisubstituted by hydroxyl and/or monosubstituted to trisubstituted by amino, or represents carboxyl-substituted alkyl having 1 to 4 carbon atoms, or phenyl which is optionally monosubstituted to trisubstituted by identical or different substituents from amongst nitro and chlorine, or represent cycloalkyl having 5 or 6 carbon atoms, or represents heterocyclic structures which are optionally saturated or unsaturated, are optionally monosubstituted to tetrasubstituted by alkyl having 1 to 4 carbon atoms or hydroxyl, and have 1 to 3 identical or different heteroatoms, and a total of 5 or 6 ring members, and $R^3$ represents hydrogen, alkyl, having 1 to 6 carbon atoms, $NH_2$,

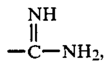

benzyl, or hydroxyalkyl having 1 to 3 carbon atoms, with the exception of the mono-, di- and triethanolamine compounds, or $R^1$ and $R^2$ together with the nitrogen atom at which they are located, form a 5-membered or 6-membered ring which can optionally contain further heteroatoms, and can optionally be substituted by keto groups or fused-on 5-membered or 6-membered rings and/or alkyl having 1 to 4 carbon atoms, with the exception of the pyridine ring which is optionally mono- or disubstituted by methyl.

8 Claims, No Drawings

OTHER PUBLICATIONS

Chemical Abstracts, vol. 82, No. 17, Apr. 28, 1975, p. 141, Abstract 107525v, "Fungicide Containing Quaternary Ammonium Saccharinate."
Chemical Abstracts, vol. 79, No. 15, Oct. 15, 1973, p. 105, Abstract 88317y, "Fungicides Containing Saccharin Derivatives for Agricultural Use."
Chemical Abstracts, vol. 79, No. 21, Nov. 26, 1973, p. 86, Abstract 122557p, "Soil Amendments."
Central Patents Index, Basic Abstracts Journal, Japan, Week T12, Class C, Mar. 1972, Abstract 19817T-C, "Controlling Plant-Disease . . . ".

SALTS OF 2-KETO-2H, 3H-1,2-BENZISOTHIAZOLE 1,1-DIOXIDE AS MICROBICIDES

The present invention relates to the use of known salts of 3-keto-2H, 3H-1,2-benzisothiazole 1,1-dioxide as microbicides, especially as fungicides and bactericides.

The use of salts of 3-keto-2H, 3H-1,2-benzisothiazole 1,1-dioxide as sweeteners, for example the monoethanolamine salts, is already known (see, for example, U.S. Pat. No. 3,325,475).

3-Alkenyloxy-1,2-benzisothiazole 1,1-dioxides, such as for example, 3-allyloxy-1,2-benzisothiazole 1,1-dioxide, as well as their action in the field of plant protection, especially as rice fungicides are also known (see Japanese Pat. No. 7,014,301; C.A. 73:45500 m).

However, under certain conditions, the action of these substances may not always be completely satisfactory in some fields of use.

Pyridine salts which are optionally mono- or disubstituted by methyl and have fungicidal properties are also known (see Japanese Pat. No. 40-022620).

Ammonium compounds of 3-keto-2H, 3H-1,2-benzisothiazole 1,1-dioxide, such as the ammonium, dimethyl-alkylbenzyl-ammonium and hydroxyethylammonium compounds, as well as salts are also known. They have a large variety of uses, for example as disinfectants and as fungicides or bactericides in the plant protection sector (see U.S. Pat. No. 3,280,137, Jp. No. 52 105-216, Jp. No. 4 8022-624 and Jp. No. 7 209 428).

It has been found that the salts of the 3-keto-2H, 3H-1,2-benzisothiazole 1,1-dioxide of the formula (I)

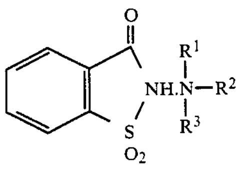

(I)

in which $R^1$ represents hydrogen, alkyl having 1 to 18 carbon atoms, or alkyl which has 1 to 6 carbon atoms and is optionally monosubstituted to trisubstituted by hydroxyl and/or monosubstituted to trisubstituted by amino, or represents carboxyl-substituted alkyl having 1 to 4 carbon atoms, or phenyl which is optionally monosubstituted to trisubstituted by identical or different substituents from amongst nitro and chlorine, or represents cycloalkyl having 5 to 6 carbon atoms, or represents heterocyclic structures which are optionally saturated or unsaturated, are optionally monosubstituted to tetrasubstituted by alkyl having 1 to 4 carbon atoms or hydroxyl, and have 1 to 3 identical or different heteroatoms, such as nitrogen and oxygen, and a total of 5 to 6 ring members.

$R^2$ represents alkyl 1 to 18 carbon atoms, or alkyl which has 1 to 6 carbon atoms and is optionally monosubstituted to trisubstituted by hydroxyl and/or monosubstituted to trisubstituted by amino, or represents carboxyl-substituted alkyl having 1 to 4 carbon atoms, or phenyl which is optionally monosubstituted or trisubstituted by identical or different substituents from amongst nitro and chlorine, or represents cycloalkyl having 5 to 6 carbon atoms, or represents heterocyclic structures which are optionally saturated or unsaturated, are optionally monosubstituted or tetrasubstituted by alkyl having 1 to 4 carbon atoms or hydroxyl, and have 1 to 3 identical or different heteroatoms, such as nitrogen and oxygen, and a total of 5 to 6 ring members.

$R^3$ represents hydrogen, alkyl having 1 to 6 carbon atoms, $NH_2$,

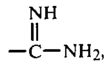

benzyl, or hydroxyalkyl having 1 to 3 carbon atoms, with the exception of the mono-, di- and triethanolamine compounds, or $R^1$ and $R^2$, together with the nitrogen atom at which they are located, form a 5-membered or 6-membered ring which can optionally contain further heteroatoms, such as nitrogen or oxygen, and can optionally be substituted by keto groups or fused-on 5-membered or 6-membered rings and/or alkyl having 1 to 4 carbon atoms, with the exception of the pyridine ring which is optionally mono- or disubstituted by methyl, which salts are known as, for example, sweeteners, possess fungicidal and bactericidal properties.

Furthermore, it has been found that the compound of the formula (IA)

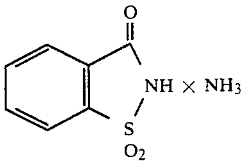

(IA)

has excellent action in particular against the causative organism of fire blight.

Surprisingly, the salts of the 3-keto-2-H, 3H-1,2-benzisothiazole, 1,1-dioxide of the general formula (I) have a higher microbicidal activity than the compound 3-allyloxy-1,2-benzisothiazole 1,1-dioxide, which is known from the prior art and is a compound with the same direction of action.

The use, according to the invention, of the salts of the 3-keto-2H, 3H-1,2-benzisothiazole dioxide thus represents an enrichment of the art.

Formula (I) gives a general definition of the salts of the 3-keto-2H, 3H-1,2-benzisothiazole 1,1-dioxide which are to be used according to the invention.

Preferred compounds of the formula (I) are those in which $R^1$ represents hydrogen, alkyl having 1 to 18 carbon atoms, in particular methyl, ethyl, n- and isopropyl, n-, sec.-, tert.- and iso-butyl, neopentyl, isooctyl, dodecyl, tetradecyl and stearyl, hydroxyalkyl having 1 to 3 carbon atoms, aminoalkyl having 1 to 3 carbon atoms, in particular 2-aminoalkyl, carboxyalkyl having 1 to 3 carbon atoms in the alkyl part, in particular carboxymethyl, 2-carboxyethyl and 1-carboxyethyl, or phenyl which is optionally monosubstituted or disubstituted by identical or different substituents from amongst nitro and chlorine, in particular 3-nitrophenyl, 4-nitrophenyl, 3-dichlorophenyl, or represents cyclopentyl or cyclohexyl, or represents optionally saturated or unsaturated 5-membered of 6 membered heterocyclic structures which have 1 to 3 nitrogen and/or oxygen atoms and are optionally monosubstituted to tetrasubstituted by alkyl having 1 to 3 carbon atoms or monosubstituted to tetrasubstituted by hydroxyl, in particular the pyridine, pyrimidine, 4-methylpyrimidine, 1,2,4- triazole, 1,2,3-triazole, tetrahydropyran and tetrahydroxytetrahydropyran radicals.

$R^2$ represents alkyl having 1 to 18 carbon atoms, in particular methyl, ethyl, n- and iso-propyl, n-, sec.-, tert.- and iso-butyl, neopentyl, isooctyl, dodecyl, tetradecyl and stearyl, hydroxyalkyl having 1 to 3 carbon atoms, aminoalkyl having 1 to 3 carbon atoms, in particular 2-aminoethyl, carboxyethyl having 1 to 3 carbon atoms in the alkyl part, in particular carboxymethyl, 2-carboxyethyl and 1-carboxyethyl, or phenyl which is optionally monosubstituted or disubstituted by identical or different substituents from amongst nitro and chlorine, in particular 3-nitrophenyl, 4-nitrophenyl, 3-chlorophenyl, 4-chlorophenyl, 3,4-dichlorophenyl and 2,6-dichlorophenyl, or represents cyclopentyl or cyclohexyl, or represents optionally saturated or unsaturated 5-membered or 6-membered heterocyclic structures which have 1 to 3 nitrogen and/or oxygen atoms and are optionally monosubstituted to tetrasubstituted by alkyl having 1 to 3 carbon atoms or monosubstituted to tetrasubstituted by hydroxy, in particular the pyridine, pyrimidine, 4-methylpyrimidine, 1,2,4-triazole, 1,2,3-triazole, tetrahydropyran and tetrahydroxytetrahydropyran radicals, or $R^1$ and $R^2$, together with the nitrogen atom at which they are located, form a 5-membered or 6-membered saturated or unsaturated ring which optionally can contain further nitrogen or oxygen atoms and can optionally be substituted by keto groups or fused-on 5-membered or 6-membered rings and/or alkyl having 1 to 3 carbon atoms, in particular the morpholine, imidazole, 2-methylimidazole, pyrazole, imidazolidine, 2-iso-propyl-3-methyl-imidazolidine, piperidine, piperazinyl, 1-methylpiperazinyl, 2,2,6,6-tetramethylpiperidine, 2,2,6,6-tetramethyl-4-keto-piperidine, tetrahydrooxazole, tetrahydro-2-isopropyloxazole and pyrrole radicals, and $R^3$ represents hydrogen, alkyl having 1 to 6 carbon atoms, in particular methyl, ethyl, n- and iso-propyl, n-, sec.-, tert.- and iso-butyl, pentyl and hexyl, amino, benzyl, hydroxyalkyl having 1 to 3 carbon atoms, and

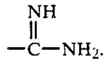

The following may be mentioned as examples of the amine component:

Methylamine, diethylamine, triethylamine, methylethylamine, isopropylamine, neopentylamine, stearylamine, cyclopentylamine, cyclohexylamine, 2-aminopyridine, 3-amino-1,2,4-triazole, morpholine, piperidine, pyrrolidine, piperazine, imidazole, pyrazole, 1,2,4-triazole, 1,2,3-triazole, imidazoline, 2-isopropylimidazoline, 2-isopropyloxazolidine, N-methylpiperidine, N-methylpiperazine, N,N'-dimethylpiperazine, N-methylpyrrolidine, hexahydro-1H-azepine, 1,4,5,6-tetrahydro-1,2-dimethylpyrimidine, triethylenediamine, 1H-benzimidazole, 1,5-diazabicyclo-[4.3.0]-non-5-ene, 1,8-diazabicyclo-[5.4.0]-undec-7-ene, 2,2,6,6-tetramethylpiperidin-4-one, aminoethanol, 1-hydroxymethyl-amine, 2-amino-2-deoxyglucose, glucosylamine, 1-amino-1-deoxysorbitol, trishydroxyethylamine, ethylenediamine, hydrazine or guanidine.

If one of the amine components contains several amino functions, both mono- and di- or polysaccharates can be isolated.

The substances to be employed as the amine component include the so-called blocked amines which, in an aqueous or alcoholic medium, decompose into the amine and the blocking component. Examples of these are N-trimethylsilylmorpholine, hexamethyldisilazane, piperidine-N-carboxylic acid triazolide and methyl-(4-nitrophenyloxycarbonyl)-amine. Accordingly, the customary hydrolyzable blocking groups, such as amidazolylcarbonyl, pyrazolylcarbonyl or triazolylcarbonyl, phenoxycarbonyl or 4-nitrophenoxycarbonyl or trialkylsilyl, are suitable for amines.

The salts of the 3-keto-2H, 3H-1,2-benzisothiazole 1,1-dioxide of the formula (I) which are to be used according to the invention are known. They are obtained, for example, when 3-keto-2H, 3H-1,2-benzisothiazole 1,1-dioxide of the formula (II)

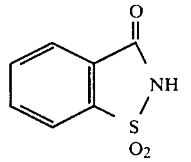

(II)

is mixed with amines of the formula (III)

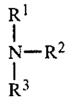

(III)

in which $R^1$ to $R^3$ have the meaning given above, if appropriate in the presence of a suitable solvent, such as, for example, water, alcohols or dimethylformamide, at elevated temperatures, in particular between 40° C. and 70° C. [see, for example, Jap. No. 13 076 (1965); Jap. 15 634 (1963); and U.S. Pat. No. 3,325,475].

The salts can also be prepared in the absence of solvents, by stirring, melting or, in the case of gaseous amine components, by gassing.

In a particular embodiment in which the blocked amines are used, solvents, such as water or alcohols, must be present as reactants.

The active compounds which can be used according to the invention exhibit a powerful microbicidal action and can be employed in practice for combating undesired micro-organisms. The active compounds are suitable for use as plant protection agents, in particular as fungicides and bactericides.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some organisms which cause fungal and bacterial diseases and which fall under the general headings listed above may be mentioned by way of example but without imposing any restriction:

Botrytis species, such as, for example, *Botrytis cinerea;*

Plasmopara species, such as, for example, *Plasmopara viticola,*

Uromyces species, such as, for example, *Uromyces appendiculatus,*

Sphaerotheca species, such as, for example, *Sphaerotheca fuliginea,*

Venturia species, such as, for example, *Venturia inaequalis,*

Podosphaera species, such as, for example, *Podosphaera leucotricha,*

Phytophthora species, such as, for example, *Phytophthora infestans,*

Erysiphe species, such as, for example, *Erysiphe graminis,*

Puccinia species, such as, for example, *Puccinia redondita,*

Fusarium species, such as, for example, *Fusarium culmorum,*

Ustilago species, such as, for example, *Ustilago nuda* or *avenae,*

Septoria species, such as, for example, *Septoria nodorum,*

Tilletia species, such as, for example, *Tilletia caries,*

Xanthomonas species, such as, for example, *Xanthomonas oryzae,*

Pseudomonas species, such as, for example, *Xanthomonas lachrymans,*

Erwinia species, such as, for example, *Erwinia amylovora,*

Pyricularia species, such as, for example, *Pyricularia oryzae,*

Pellicularia species, such as, for example *Pellicularia sasakii,*

Pyrenophora species, such as, for example, *Pyrenophora teres* (conidia form: Drechslera, Syn: Helminthosporium), Leptosphaeria species, such as, for example, *Leptosphaeria nodorum,*

Cochliobolus species, such as, for example, *Cochliobolus sativus,*

(conidia form: Drechslera, Syn: Helminthosporium) and

Cercospora species, such as, for example, *Cercospora canescens.*

The good toleration by plants, of the active compounds, at the concentrations required for combating plant diseases, permits treatment of above-ground parts of plants, of vegetative propagation stock and seeds, and of the soil.

The active compounds which can be used according to the invention can be converted to the customary formulations, such as solutions, emulsions, suspensions, powders, foams, pastes, granules, aerosols, very fine capsules in polymeric substances and in coating compositions for seed, and ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example a ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds which can be used according to the invention can be present in the formulations as a mixture with other known active compounds, such as fungicides, insecticides, acaricides and selective herbicides, and as mixtures with fertilizers and growth regulators.

The active compounds which can be used according to the invention can be used as such, in the form of their formulations or in the use forms prepared therefrom, such as ready-to-use solutions, emulsifiable concentrates, emulsions, foams, suspensions, wettable powders, pastes, soluble powders, dusting agents and granules. They are used in a customary manner, for example by watering, spraying, atomizing, scattering, dusting, foaming, painting, etc. It is also possible to apply the active compounds by the ultra low volume method, or to inject the active compound formulation or in the active compound itself into the soil. It is also possible to treat the seed of the plants.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.0001 to 0.02%, are required at the place of action.

The good action against the causative organism *Erwinia amylovora* which causes fire blight should be particularly singled out; here the unsubstituted ammonium compound should be mentioned in particular; they are also used with good success for combating rice diseases, such as, for example, the blast disease of rice causative organism (*Pyricularia oryzae*) or the bacteriosis of rice causative organism (*Xanthomonas oryzae*). The good action in combating cereal diseases, caused for example by *cochliobolus sativus* or *Pyrenophora teres,* should also be singled out.

USE EXAMPLES

The following compounds are employed as comparative substances:

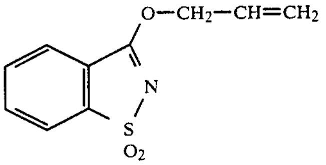

(A)

and $$3\times Cu(OH)_2.CuCl_2 \text{ or } Cu_2(OH_3)Cl \qquad (B)$$

EXAMPLE A

Pyricularia test (rice)/protective

Solvent: 12.5 parts by weight of acetone

Emulsifier: 0.3 parts by weight of alkylaryl polyglycol ether

To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae.* The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following examples:

TABLE A

Pyricularia test (rice)/protective

| Active compounds | Active compound concentration in % | Disease infestation as a percentage of the untreated control |
|---|---|---|
| 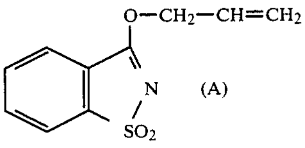 (A) (known) | 0.025 | 25 |
| 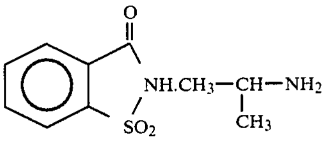 | 0.025 | 0 |
| 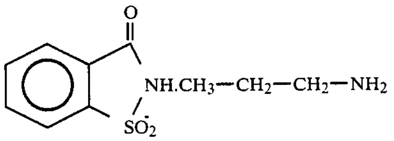 | 0.025 | 10 |
| 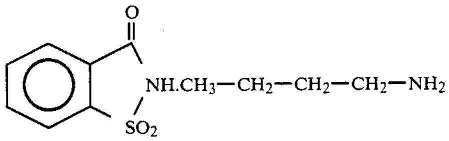 | 0.025 | 10 |
| 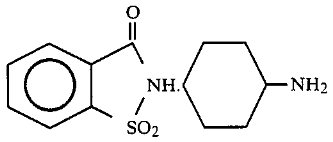 | 0.025 | 0 |

TABLE A-continued
Pyricularia test (rice)/protective
| Active compounds | Active compound concentration in % | Disease infestation as a percentage of the untreated control |
|---|---|---|
| 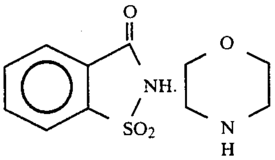 | 0.025 | 10 |
| 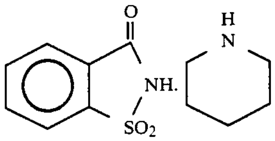 | 0.025 | 10 |
| 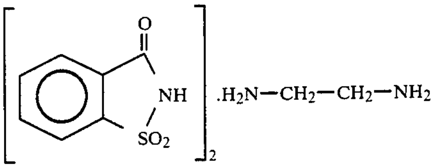 | 0.025 | 10 |
| 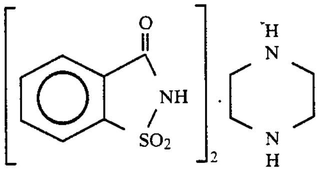 | 0.025 | 10 |
| 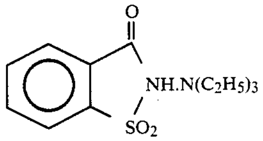 | 0.025 | 10 |
| 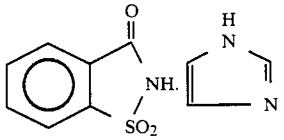 | 0.025 | 0 |
| 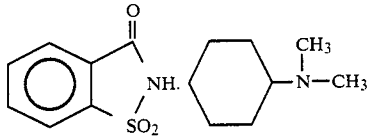 | 0.025 | 10 |
| 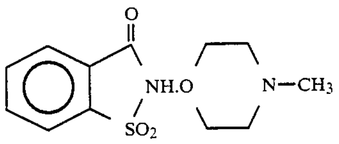 | 0.025 | 0 |
| 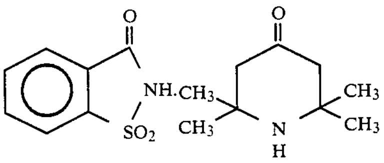 | 0.025 | 0 |

TABLE A-continued

Pyricularia test (rice)/protective

| Active compounds | Active compound concentration in % | Disease infestation as a percentage of the untreated control |
|---|---|---|
| 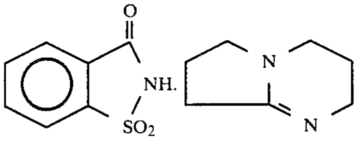 | 0.025 | 0 |
| 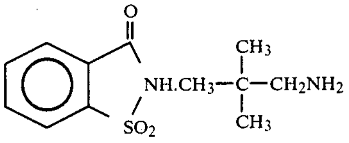 | 0.025 | 10 |
| 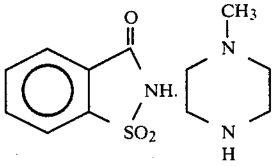 | 0.025 | 10 |
| 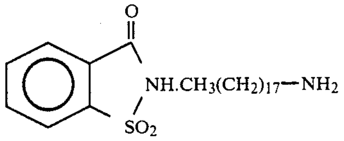 | 0.025 | 10 |
| 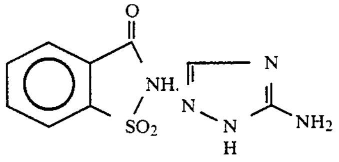 | 0.025 | 20 |
| 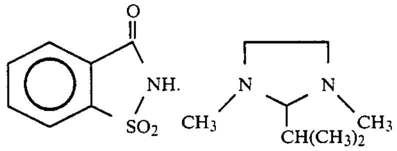 | 0.025 | 10 |

EXAMPLE B

Pyricularia test (rice)/systemic

Solvent: 12.5 parts by weight of acetone

Emulsifier: 0.3 parts by weight of alkylaryl polyglycol ether

To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae.* Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following examples:

TABLE B
| Active compounds | Pyricularia test (rice)/systemic | |
|---|---|---|
| | Amount applied, in mg of active compound per 100 $cm^2$ | Disease infestation as a percentage of the untreated control |
| 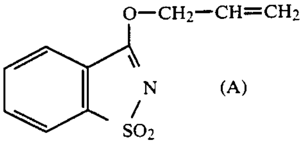 (A) (known) | 100 | 50 |
| 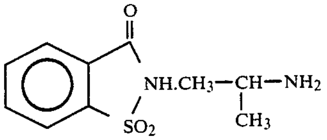 | 100 | 30 |
| 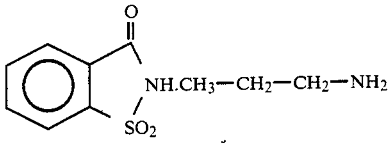 | 100 | 10 |
| 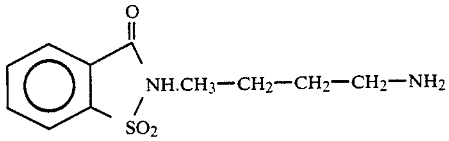 | 100 | 22 |
| 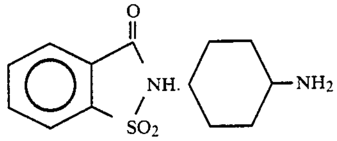 | 100 | 30 |
| 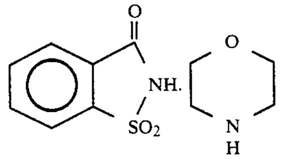 | 100 | 20 |
| 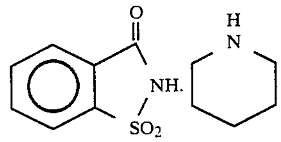 | 100 | 20 |
| 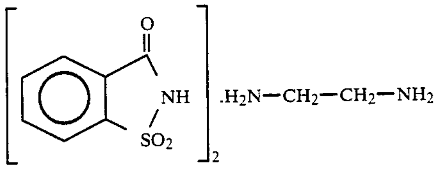 | 100 | 20 |
| 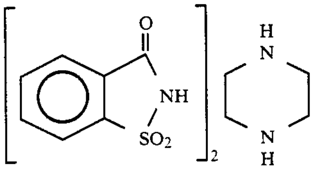 | 100 | 20 |

TABLE B-continued
| Active compounds | Pyricularia test (rice)/systemic<br>Amount applied, in mg of active compound per 100 cm$^2$ | Disease infestation as a percentage of the untreated control |
|---|---|---|
| 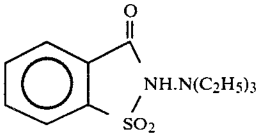 | 100 | 20 |
| 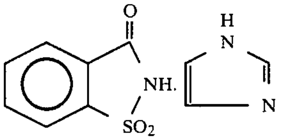 | 100 | 0 |
| 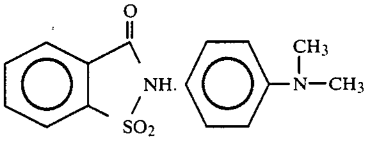 | 100 | 20 |
| 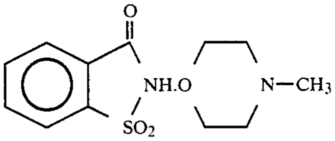 | 100 | 0 |
| 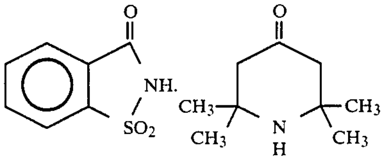 | 100 | 10 |
| 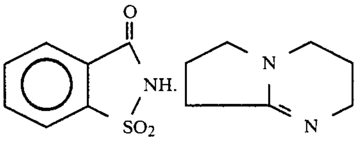 | 100 | 10 |
| 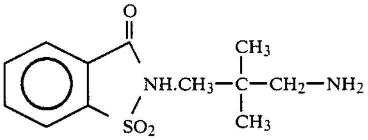 | 100 | 20 |
| 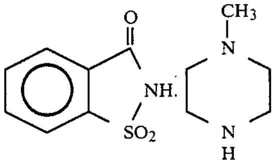 | 100 | 20 |
| 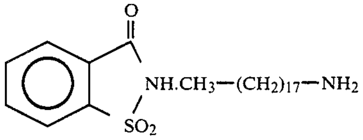 | 100 | 20 |
| 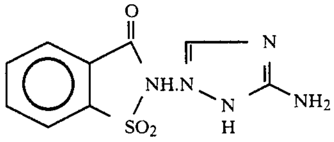 | 100 | 0 |

TABLE B-continued

| Active compounds | Pyricularia test (rice)/systemic<br>Amount applied, in mg of active compound per 100 $cm^2$ | Disease infestation as a percentage of the untreated control |
|---|---|---|
| 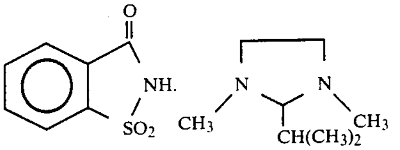 | 100 | 20 |

EXAMPLE C

*Xanthomonas oryzae* test/bacteriosis/rice/systemic
Solvent: 121.25 parts by weight of acetone
Emulsifier: 3.75 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for systemic properties, standard soil in which young plants have been grown is watered with 100 ml of the preparation of active compound. 3 days after the treatment, the plants are inoculated with an aqueous suspension of *Xanthomonas oryzae* by prickling. Thereafter, plants remain in a greenhouse at 24° to 26° C. and 70–80% relative atmospheric humidity for 14 days until they are evaluated.

In this test, a clearly superior activity compared with the prior art is shown, for example, by the compounds according to the following preparation examples:

TABLE C

| Active compounds | *Xanthomonas oryzae* test/bacteriosis/rice systemic<br>Amount applied, in mg of active compound per 100 $cm^2$ | Disease infestation as a percentage of the untreated control, systemic |
|---|---|---|
| 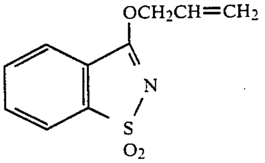<br>(A)<br>(known) | 10 | 90 |
| 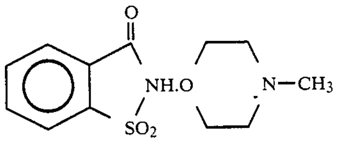 | 10 | 30 |

EXAMPLE D

*Erwinia amylovora* test/bacteriosis/apple/systemic
Solvent: 49 parts by weight of acetone
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for systemic properties, standard soil in which young plants have been grown is watered with the preparation of active compound. 3 days after the treatment, the plants are inoculated with an aqueous suspension of *Erwinia amylovora* by spraying over. After incubation for 48 hours at 100% relative atmospheric humidity, the plants remain in a climatic chamber at 24° C. and 70–80% relative atmospheric humidity for 8 days until they are evaluated.

In this test, a clearly superior activity compared with the prior art is shown, for example, by the compounds according to the following examples:

TABLE D

| Active compounds | *Erwinia amylovora* test/bacteriosis/apple/systemic<br>Amount applied, in mg of active compound per 100 $cm^2$ | Disease infestation as a percentage of the untreated control, |
|---|---|---|
| $3Cu(OH)_2.CuCl_2$ or $Cu_2(OH)_3Cl$<br>(B)<br>(known) | 10 | 80 |

TABLE D-continued

*Erwinia amylovora* test/bacteriosis/apple/systemic

| Active compounds | Amount applied, in mg of active compound per 100 $cm^2$ | Disease infestation as a percentage of the untreated control, |
|---|---|---|
| 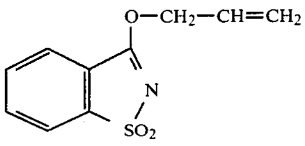 (A) (known) | 10 | 50 |
| 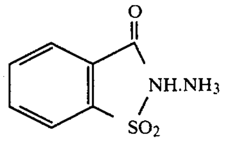 | 10 | 20 |
| 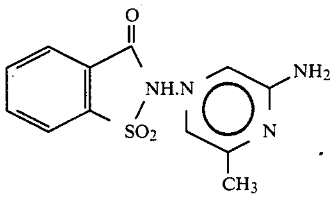 | 10 | 15 |
| 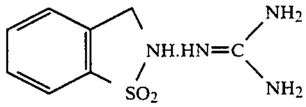 | 10 | 10 |

EXAMPLE E

*Erwinia amylovora test/bacteriosis/apple/protective*

Solvent: 49 parts by weight of acetone

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated by spraying over with an aqueous suspension of *Erwinia amylovora*. After an incubation period of 48 hours at 100% relative atmospheric humidity, the plants remain in a climatic chamber at 24° C. and 70-80% relative atmospheric humidity for 8 days until they are evaluated.

In this test, a clearly superior activity compared with the prior art is shown, for example, by the compounds according to the following examples:

TABLE E

*Erwinia amylovora* test/bacteriosis/apple/protective

| Active compounds | Active compound concentration in % | Disease infestation as a percentage of the untreated control |
|---|---|---|
| 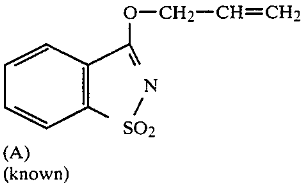 (A) (known) | 0.025 | 70 |
| 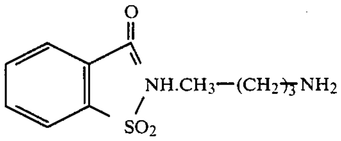 | 0.025 | 20 |
| 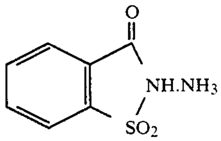 | 0.025 | 20 |

TABLE E-continued

| *Erwinia amylovora* test/bacteriosis/apple/protective | | |
|---|---|---|
| Active compounds | Active compound concentration in % | Disease infestation as a percentage of the untreated control |
| 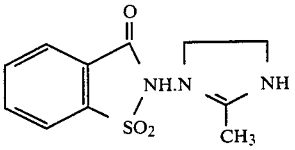 | 0.025 | 20 |

PREPARATION EXAMPLES

The examples which follow are intended to illustrate the invention further.

EXAMPLE 1

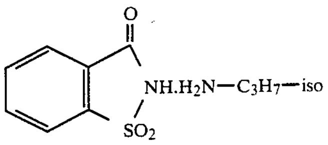

183 g (1 mol) of 3-keto-2H, 3H-1,2-benzisothiazole 1,1-dioxide are heated to 60° C. with 59 g of isopropylamine (gaseous) or with an aqueous solution containing 59 g of isopropylamine in 200 ml of n-butanol. After 10 minutes, the solvents are removed by distillation, and 242 g of the salt are obtained as an oil (100% of theory).

EXAMPLE 2

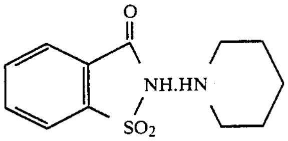

183 g (1 mol) of 3-keto-2H, 3H-1,2-benzisothiazole 1,1-dioxide and 86 g (1 mol) of piperidine are mixed in a heatable paddle mixer at 50° C. until the IR spectrum of a sample shows that the $SO_2$ band has shifted to below 1400 $cm^{-1}$ (1350–1380). The product is obtained as an oil (268 g, 100% of theory).

EXAMPLE 3

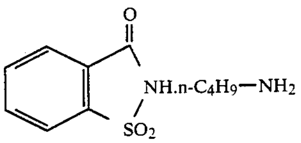

183 g (1 mol) of 3-keto-2H, 3H-1,2-benzisothiazole 1,1-dioxide and 219 g (3 mol) of n-butylamine are heated while stirring. After 10 minutes, the excess butylamine (146 g) is distilled off, the salt remaining behind as a colorless solid of melting point 88° C. (256 g, 100% of theory).

The compounds of the formula

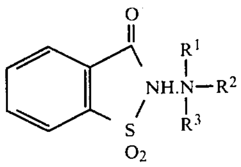

(I)

wherein the amine component is the amines below, can be prepared analogously to the examples described above:

| Example: | 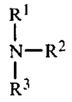 | Melting point [°C.] of the end compound of the formula (I) |
|---|---|---|
| 4 | 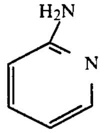 | 215 |
| 5 | 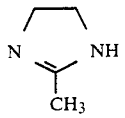 | 190 |
| 6 | 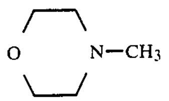 | oil |
| 7 | 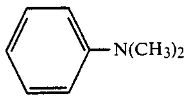 | 130 |
| 8 | 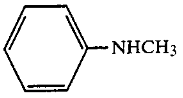 | oil |
| 9 | 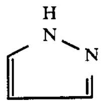 | 235 |
| 10 | 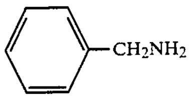 | oil |
| 11 | 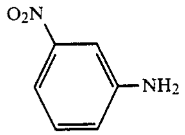 | 192 |
| 12 | 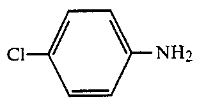 | 178 |

-continued
| Example: | 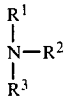 | Melting point [°C.] of the end compound of the formula (I) |
|---|---|---|
| 13 | 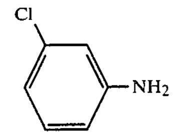 | 165 |
| 14 | 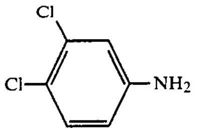 | 192 |
| 15 | 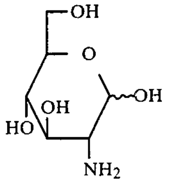 | oil |
| 16 | 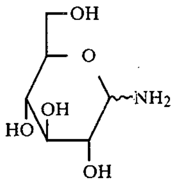 | oil |
| 17 | 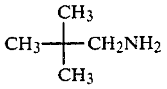 | 90 |
| 18 | 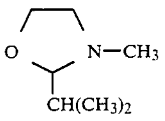 | oil |
| 19 | $H_2N—NH_2$ | 148 |
| 20 | $NH_3$ | 226 |
| 21 | 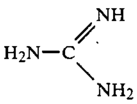 | 210 |
| 22 | $CH_3NH_2$ | 157 |
| 23 | $C_2H_5NH_2$ | 148 |
| 24 | n-$C_3H_7NH_2$ | 137 |
| 25 | i-$C_3H_7—NH_2$ | oil |
| 26 | n-$C_4H_9NH_2$ | 88 |
| 27 | $1H_2N—CH_2—CH_2—NH_2$ | oil |
| 28 | $\frac{1}{2}H_2N—CH_2—CH_2—NH_2$ | 232 |
| 29 | $(C_2H_5)_3N$ | oil |
| 30 | $CH_3—(CH_2)_{11}NH_2$ | oil |
| 31 | $CH_3—(CH_2)_{17}NH_2$ | oil |
| 32 | 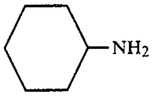 | 186 |
| 33 | 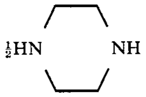 | 249 |
-continued
| Example: | 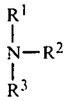 | Melting point [°C.] of the end compound of the formula (I) |
|---|---|---|
| 34 | 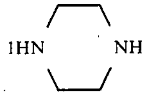 | 248 |
| 35 | 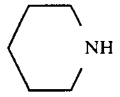 | oil |
| 36 | 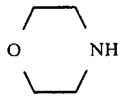 | oil |
| 37 | 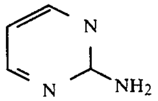 | 235 |
| 38 | 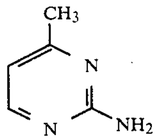 | 225 |
| 39 | 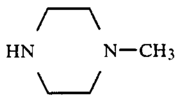 | 161 |
| 40 | 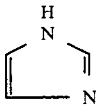 | 182 |
| 41 | 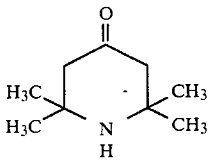 | 147 |
| 42 | 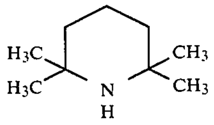 | 121 |
| 43 | 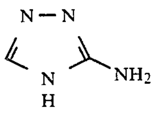 | 190 |
| 44 | 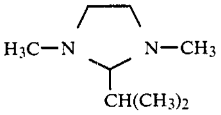 | 130 |

-continued

| Example: | 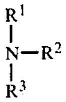 | Melting point [°C.] of the end compound of the formula (I) |
|---|---|---|
| 45 | 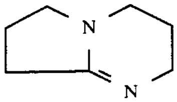 | 160 |
| 46 | $H_2N-CH_2COONa$ | 240 |
| 47 | 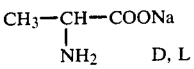 D, L | 201 |
| 48 | $H_2N-CH_2CH_2COONa$ | 186 |

It will be understood that the specification and examples are illustrative but not limitative of the present invention and that other embodiments within the spirit and scope of the invention will suggest themselves to those skilled in the art.

We claim:

1. A method of combating plant pathogenic fungi and bacteria which comprises applying to such fungi or bacteria a fungicidally or bactericidally effective amount of at least one salt of 3-keto-2H,3H-1,2-benzisothiazole 1,1-dioxide of the formula

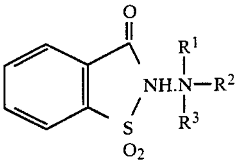

$R^1$ represents hydrogen, alkyl having 1 to 18 carbon atoms, hydroxyalkyl having 1 to 3 carbon atoms, aminoalkyl having 1 to 3 carbon atoms, carboxyalkyl having 1 to 3 carbon atoms in the alkyl part, phenyl which is optionally monosubstituted or disubstituted by nitro or chlorine, cyclopentyl or cyclohexyl, or represent pyrimidine, 4-methylpyrimidine, 1,2,4-triazole, 1,2,3-triazole, or tetrahydropyran radicals which are optionally monosubstituted to tetrasubstituted by alkyl having 1 to 3 carbon atoms or monosubstituted to tetrasubstituted by hydroxyl, $R^2$ represents alkyl having 1 to 18 carbon atoms, hydroxyalkyl having 1 to 3 carbon atoms, aminoalkyl having 1 to 3 carbon atoms, carboxyalkyl having 1 to 3 carbon atoms in the alkyl part, phenyl which is optionally monosubstituted or disubstituted by nitro or chlorine, cyclopentyl or cyclohexyl, or represent pyrimidine, 4-methyl pyrimidine, 1,2,4-triazole, 1,2,3-triazole, or tetrahydropyran radicals which are optionally monosubstituted to tetrasubstituted by alkyl having 1 to 3 carbon atoms or monosubstituted to tetrasubstituted by hydroxyl, or $R^1$ and $R^2$, together with the nitrogen atom to which they are attached, form a pyrimidine, 1,2,4-triazole, 1,2,3-triazole, tetrahydropyran or tetrahydroxy tetrahydropyran radical, and $R^3$ represents hydrogen, alkyl having 1 to 6 carbon atoms, amino, benzyl, hydroxyalkyl having 1 to 3 carbon atoms or

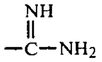

with the exception of the mono-, di- or triethanolamine compounds.

2. The method according to claim 1, in which $R^1$ represents hydrogen, methyl, ethyl, n- or iso-propyl, n-, sec.-, tert.- or iso-butyl, neopentyl, isooctyl, dodecyl, tetradecyl, stearyl, 2-aminoethyl, carboxymethyl, 2-carboxyethyl, 1-carboxyethyl, phenyl, 3-nitrophenyl, 4-nitrophenyl, 3-chlorophenyl, 4-chlorophenyl, 3,4-dichlorophenyl, 2,6-dichlorophenyl, cyclopentyl, cyclohexyl, pyrimidine, 4-methylpyrimidine, 1,2,4-triazole, 1,2,3-triazole, tetrahydropyran or tetrahydroxypyran radicals, $R^2$ represents methyl, ethyl, n- or iso-propyl, n-, sec.-, tert.- or iso-butyl, neopentyl, isooctyl, dodecyl, tetradecyl, stearyl, 2-aminoethyl, carboxymethyl, 2-carboxyethyl, 1-carboxyethyl, phenyl, 3-nitrophenyl, 4-nitrophenyl, 3-chlorophenyl, 4-chlorophenyl, 3,4-dichlorophenyl, 2,6-dichlorophenyl, cyclopentyl, cyclohexyl, pyrimidine, 4-methylpyrimidine, 1,2,4-triazole, 1,2,3-triazole, tetrahydropyran or tetrahydroxypyran radicals, or $R^1$ and $R^2$, together with the nitrogen atom to which they are attached, form pyrmidine, 1,2,4-triazole, 1,2,3-triazole, tetrahydropyran or tetrahydroxy tetrahydropyran radical, and $R^3$ represents hydrogen, methyl, ethyl, n- or iso-propyl, n-, sec.-, tert.- or iso-butyl, pentyl, hexyl, amino, benzyl or

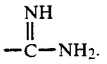

3. The method according to claim 1, wherein such salt

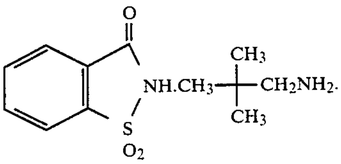

4. The method according to claim 1, wherein such salt is

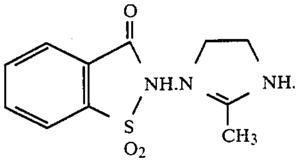

5. The method according to claim 1, wherein such salt is

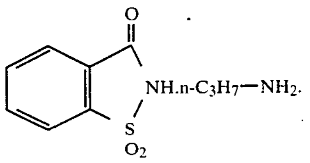
6. The method according to claim 1, wherein such salt is
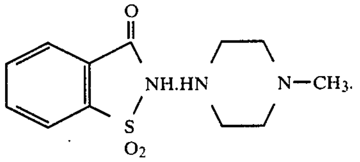
7. The method according to claim 1, wherein such salt is
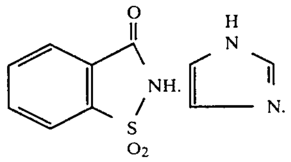
8. A method of combating the Pathogenic organism of fire blight which comprises applying to such organism, a bactericidally effective amount of a salt of 3-keto-2H, 3H-1,2-benzisothiazole 1,1-dioxide of the formula (IA)
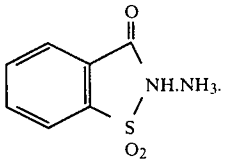
* * * * *

UNITED STATES PATENT AND TRADEMARK OFFICE
CERTIFICATE OF CORRECTION

PATENT NO. : 4,683,233

DATED : July 28, 1987

INVENTOR(S) : Herbert Salzburg, et al.

It is certified that error appears in the above-identified patent and that said Letters Patent is hereby corrected as shown below:

| | |
|---|---|
| Title Page, No. 75 "Inventors", line 3 | Delete "Varl-Heinz Kuck" and substitute --Karl-Heinz Kuck-- |
| Col. 2, line 3 | After "members" delete "." and substitute --,-- |
| Col. 3, line 2 | After "radicals" delete "." and substitute --,-- |
| Col. 6, line 8 | After "example" delete "a" |
| Col. 6, line 58 | After "or" delete "in" |
| Col. 20, line 60 | End of formula delete "$(CH_2)_3NH_2$" and substitute --$(CH_2)_3$-$NH_2$-- |
| Col. 26, line 34 | Correct spelling of --pyrimidine-- |
| Col. 26, line 46 | After "salt" insert --is-- |

Signed and Sealed this

Seventeenth Day of May, 1988

Attest:

DONALD J. QUIGG

*Attesting Officer*

*Commissioner of Patents and Trademarks*